United States Patent [19]

Bolognesi et al.

[11] Patent Number: 5,627,023
[45] Date of Patent: May 6, 1997

[54] SUPPRESSOR OF HIV REPLICATION AND TRANSCRIPTION

[75] Inventors: Dani P. Bolognesi, Durham; Chin-Ho Chen, Chapel Hill; Michael L. Greenberg; Kent Weinhold, both of Durham, all of N.C.

[73] Assignee: Duke University, Durham, N.C.

[21] Appl. No.: 38,387

[22] Filed: Mar. 29, 1993

[51] Int. Cl.$^6$ .............................. C12Q 1/02; C12Q 1/70
[52] U.S. Cl. ............................ 435/5; 435/7.24; 435/8; 435/29; 435/974
[58] Field of Search ......................... 435/8, 29, 4, 5, 435/7.24, 172.3, 974, 6; 935/59

[56] References Cited

PUBLICATIONS

Barré-Sinoussi, F. et al., 1983; Isolation of a T–Lymphotropic Retrovirus from a Patient at Risk for Acquired Immune Deficiency Syndrome (AIDS). Science 220:868–871.
Gallo, R. et al., 1984; Frequent Detection and Isolation of Cytopathic Retroviruses (HTLV–III) from Patients with AIDS and at Risk for AIDS. Science 224:500–503.
Wong-Staal, F. and Gallo, R., 1985; Human T–Lymphotropic Retroviruses. Nature 317:395–403.
Walker et al., 1986; CD8$^+$ Lymphocytes Can Control HIV Infection in Vitro by Suppressing Virus Replication. Science 234: 1563–1566.
Kannagi, M. et al., 1988; Suppression of Simian Immunodeficiency Virus Replication in Vitro By CD8+ Lymphocytes. Journal of Immunology 140(7): 2237–2242.
Tsubota, H. et al., 1989; A Cytotoxic T Lymphocyte Inhibits Acquired Immunodeficiency Syndrome Virus Replication in Peripheral Blood Lymphocytes. J. Exp. Med. 169:4121–1434.
Walker, C. and Levy, J., 1989; A Diffusible Lymphokine Produced by CD8$^+$ T Lymphocytes Suppresses HIV Replication. Immunology 66:628–630.
Tsubota, H. et al., 1989; CD8$^+$ CD4$^-$ Lymphocyte Lines Can Harbor the AIDS Virus In Vitro. Journal of Immunology 143(3):858–863.
Cullen, B. and Greene, W., 1989; Regulatory Pathways Governing HIV Replication. Cell 58:423–426.
Walker, C. et al., 1989; CD8$^+$ T Lymphocyte Control of HIV Replication in Cultured CD4$^+$ Cells Varies among Infected Individuals. Cellular Immunology 119:470–475.
Brinchmann, J. et al., 1989; Reliable Isolation of Human Immunodeficiency Virus from Cultures of Naturally Infected CD4$^+$ T Cells. Journal of Virological Methods 25:293–300.
Brinchmann, J. et al., 1990; CD8$^+$ T Cells Inhibit HIV Replication in Naturally Infected CD4$^+$ T Cells, Evidence for a Soluble Inhibitor. J. Immunol. 144:2961–2966.
Kannagi, M. et al., 1990; Interference with Human Immunodeficiency Virus (HIV) Replication by CD8$^+$ T Cells in Peripheral Blood Leukocytes of Asymptomatic HIV Carriers In Vitro. Journal of Virology 64(7):3399–3406.

Wiviott, L. et al., 1990; CD8$^+$ Lymphocytes Suppress HIV Production by Autologous CD4$^+$ Cells without Eliminating the Infected Cells from Culture. Cellular Immunology 128:628–634.
Castro, B., 1991; Suppression of Human Immunodeficiency Virus Replication by CD8$^+$ Cells from Infected and Uninfected Chimpanzees. Cellular Immunology 132:246–255.
Mackewicz, C., et al., 1991; CD8$^+$ Cell Anti–HIV Activity Correlates with the Clinical State of the Infected Individual. J. Clin. Invest. 87:1462–1466.
Brinchmann, J. et al., 1991; In Vitro Replication of HIV–1 in Naturally Infected CD4$^+$ T Cells is Inhibited by rIFN$\alpha_2$ and by a Soluble Factor Secreted by Activated CD8$^+$ T Cells, But Not By rIFN$_\beta$, rIFN$_\delta$, or Recombinant Tumor Necrosis Factor–$\alpha$. Journal of Acquired Immune Deficiency Syndrome 4(5):480–488.
Walker, C. et al., 1991; CD8$^+$ Cells from HIV–1–Infected Individuals Inhibit Acute Infection by Human and Primate Immunodeficiency Viruses. Cellular Immunology 137:420–428.
Walker, C. et al., 1991; Inhibition of Human Immunodeficiency Virus Replication in Acutely Infected CD4$^+$ Cells by CD8$^+$ Cells Involves a Noncytotoxic Mechanism. J. Virology 65(11):5921–5927.
Copeland et al., "CD8 T Lymphocyte–Mediated Suppression of HIV–1 LTR–Mediated Transcription Shows No Correlation With Clinical Stage of Disease or Health Status," *Eleventh Int.'l. Conference on AIDS, Vancouver*, Jul. 7–12, 1996, p. 227, Abstract No. Tu.A.395.
Powell, J. D. et al. 1991. *Ann. N.Y. Acad. Sci. USA* vol 636 pp. 360–363.
Powell, J. D. et al. 1993. *Clin. Exp. Immunol.* vol 91 pp. 473–481.
Mackewicz, C. et al. 1992. *AIDS Res. Human Retro Vir.* vol 8 pp. 1039–1050.
Stein, D.S. et al. 1993. *Clinical Infections Diseases* vol 17 pp. 749–771.
Carson, K.L., 1994. *Genetic Engineering News* vol 14 No 9 pp. 1, 24, 34.
Powell, J.D. et al. 1990. *Sym. Non hum. Primate Models AIDS* v. 8 p. 43.
Mackewicz, C. et al. 1991. *Int. Conf. AIDS* vol 7 No. 2 p. 74.

*Primary Examiner*—Robert D. Budens
*Attorney, Agent, or Firm*—Pennie & Edmonds

[57] ABSTRACT

The present invention relates to a bioactive molecule, herein referred to as the CD8 suppressor molecule, that is produced by the CD8 subset of human T-lymphocytes and suppresses type-1 human immunodeficiency virus (HIV-1) replication through inhibition of viral transcription. The invention relates to isolation of clonal CD8 cells lines that produce the antiviral activity and the development of an assay system for detection of the antiviral activity. The clonal cell lines and the assay system, described herein, may be utilized to purify, characterize and clone the CD8 suppressor molecule. The CD8 suppressor molecule may have therapeutic applications for treatment of diseases associated with HIV-1 infection.

5 Claims, 5 Drawing Sheets

SUPPRESSOR OF HIV REPLICATION AND TRANSCRIPTION

This invention was made with government support under grant 5-RO1-AT32393, 5-RO1-AI29852, and 5-P30-AI28662 awarded by the NIAID. The government has certain rights in this invention.

TABLE OF CONTENTS

1. Introduction
2. Background of the Invention
3. Summary of the Invention
4. Description of the Figures
5. Detailed Description of the Invention
   - 5.1. CD8+ Suppressor Molecular Inhibits HIV-1 Viral Transcription
   - 5.2. Subsets of CD8+ Cells Express Anti-Viral Activity
   - 5.3. Purification and Characterization of CD8+ Suppressor Molecule
   - 5.4. Cloning of CD8+ Suppressor Molecule
   - 5.5. Uses of the CD8+ Suppressor Molecule
6. Example: CD8 Suppressor Activity Inhibits HIV-1 Replication
   - 6.1. Materials and Methods
     - 6.1.1. Reverse Transcriptase Assays
     - 6.1.2. HIV-1 LTR CAT Constructs
     - 6.1.3. Transfections and CAT Assays
   - 6.2. Results
     - 6.2.1. CD8 Cells Inhibit HIV-1 Replication in CD4 HIV Infected Cells
7. Example: Isolation of CD8 Clonal Cells Expressing the Anti-HIV-1 Suppressor Molecule
   - 7.1. Materials and Methods
     - 7.1.1. Establishment of CD8+ Cell Clones
     - 7.1.2. Assay of Transcriptional Inhibition Activity in CD8 Cell Clones
   - 7.2. Results
     - 7.2.1. Establishment of CD8 Cell Clones Expressing the HIV-1 Suppressor Molecule
8. Deposit of Microorganisms

INTRODUCTION

The present invention relates to a bioactive molecule, herein referred to as the CD8 suppressor molecule, that is produced by the CD8 subset of human T-lymphocytes and suppresses human immunodeficiency virus (HIV) replication through inhibition of viral transcription. The invention relates to isolation of clonal CD8 cells lines that produce the antiviral activity and the development of an assay system for detection of the antiviral activity. The clonal cell lines and the assay system, described herein, may be utilized to purify, characterize and clone the CD8 suppressor molecule. The CD8 suppressor molecule may have therapeutic applications for treatment of diseases associated with HIV infection.

BACKGROUND OF THE INVENTION

The type-1 human immunodeficiency virus (HIV-1) has been implicated as the primary cause of the slowly degenerate disease of the immune system termed acquired immune deficiency syndrome (AIDS) (Barré-Sinoussi, F. et al., 1983 Science 220:868–70; Gallo, R. et al. 1984, Science 224:500-3). Infection of the CD4+ subclass of T-lymphocytes with the HIV-1 virus leads to depletion of this essential lymphocyte subclass which inevitably leads to opportunistic infections, neurological disease, neoplastic growth and eventually death. HIV-1 infection and HIV-1 associated diseases represent a major health problem and considerable attention is currently being directed towards the successful design of effective therapeutics.

HIV-1 is a member of the lentivirus family of retroviruses (Teich, N. et al., 1984 In RNA Tumor Viruses ed. R. Weiss, N. Teich, H. Varmus, J. Coffin CSH Press, pp. 949–56). The life cycle of HIV-1 is characterized by a period of proviral latency followed by active replication of the virus. The primary cellular target for the infectious HIV-1 virus is the CD4 subset of human T-lymphocytes. Targeting of the virus to the CD4 subset of cells is due to the fact that the CD4 cell surface protein acts as the cellular receptor for the HIV-1 virus (Dalgleish, A. et al., 2984, Nature 312:763-67; Klatzmann et al. 1984, Nature 312:767-68; Maddon et al. 1986 Cell 47:333-48).

After binding to the cell surface, the HIV-1 virion becomes internalized, and once inside the cell, the viral life cycle begins by conversion of the RNA genome into linear DNA molecules. This process is dependent on the action of the virally encoded reverse transcriptase. Following replication of the viral genome, the linear DNA molecule integrates into the host genome through the action of the viral integrase protein, thus establishing the proviral form of HIV-1.

During the early phase of proviral expression, transcription of the viral genome results in expression of regulatory proteins such as Tat, Nef and Rev. Transcriptional activation of the proviral DNA is mediated through the viral 5' LTR sequences (long terminal repeats). The initial low level of viral transcription is dramatically increased by the HIV encoded transactivator protein termed tat (transactivator protein) (Cullen, B. R. et al. 1989, Cell 58:423-26). The Rev protein promotes the transition from the early phase expression of regulatory proteins to late phase expression of structural proteins. Assembly of newly synthesized viral particles is followed by budding of virus particles from the cell membrane allowing the virus to infect new cells.

The HIV-1 virus is capable of establishing a latent state of infection for prolonged periods of time. Individuals infected with the human immunodeficiency virus may remain clinically healthy for long periods of time, with the estimated average length of the asymptomatic period between primary HIV infection and the progression to AIDS and increase in viral replication being approximately 8 to 10 years. Several possibilities have been proposed to explain the maintenance of the low levels of viral replication during this period of latency. It is generally believed that the humoral immune response to HIV-1 is not sufficiently protective against progression of the disease and attention has, therefore, turned to the possibility that the T-lymphocyte population of cells may directly inhibit HIV-1 replication.

A number of groups have recently noted that the CD8+ subset of T-lymphocytes have the ability to inhibit the replication of HIV-1 in vitro (Walker, C. M. et al., 1989, Cellular Immunology 119:470–475; Kannagi, M. et al. 1990, J. Virology 64:3399–3406; Walker, C. M. et al., 1991 J. Virology 65:5921–5927). For example, addition of CD8 cells to naturally HIV-1 infected CD4 cell cultures was found to inhibit the replication of HIV-1 in the infected cultures in a dose dependent manner. (Ref. supra). Furthermore, the inhibitory effect is not dependent on cell-cell contact as an inhibitory effect is observed across a semi-permeable membrane suggesting that the CD8 suppressor activity is a soluble inhibitor of HIV-1 replication. (Ref. supra). To date, the molecular identity of the CD8 suppressor molecule, or a combination of factors, as well as the mechanism by which it exerts its antiviral effect remains undefined.

SUMMARY OF THE INVENTION

The present invention relates to a soluble molecule secreted by the CD8 subclass of T-lymphocytes and to the ability of that molecule to markedly inhibit HIV viral replication. The invention further relates to the observation that the mechanism by which the suppressor molecule exerts its antiviral activity is at the level of inhibition of viral gene expression from the viral LTR promoter.

In a principle embodiment, the invention is directed to an assay system to be used for detection of the HIV inhibitory activity, whereby the HIV LTR sequence is cloned adjacent to a reporter gene such as the CAT gene. In such an assay system, the presence of the suppressor molecule may be determined by measuring the levels of reporter gene product.

The present invention further relates to the isolation and characterization of $CD8^+$ cell clones that produces the antiviral activity of interest. Such cell clones may be advantageously used for large scale isolation and characterization of the suppressor molecule and/or as a source of mRNA for construction of cDNA libraries that may be used for cloning the suppressor molecule. The invention also relates to the use of the suppressor molecule in the treatment of HIV-infection.

DETAILED DESCRIPTION OF THE INVENTION

The present invention relates to a protein produced by the CD8 subclass of T-lymphocytes that is able to inhibit HIV viral replication. The invention further relates to an assay system for detection of the antiviral activity wherein a reporter gene is cloned adjacent to the HIV viral LTR sequences. The development of the assay system is based on the observation that the suppressor molecule inhibits transcription of genes linked to the HIV LTR promoter sequences. In addition, the invention is directed to the isolation of clonal CD8 cells that expresses the antiviral activity. Such cell lines may be advantageously used for purification and characterization of the CD8 suppressor molecule and/or for cloning of the CD8 suppressor molecule. The CD8 suppressor molecule may be used therapeutically to inhibit HIV-replication.

SUPPRESSOR MOLECULAR INHIBITS HIV-1 VIRAL TRANSCRIPTION

Figure 1:
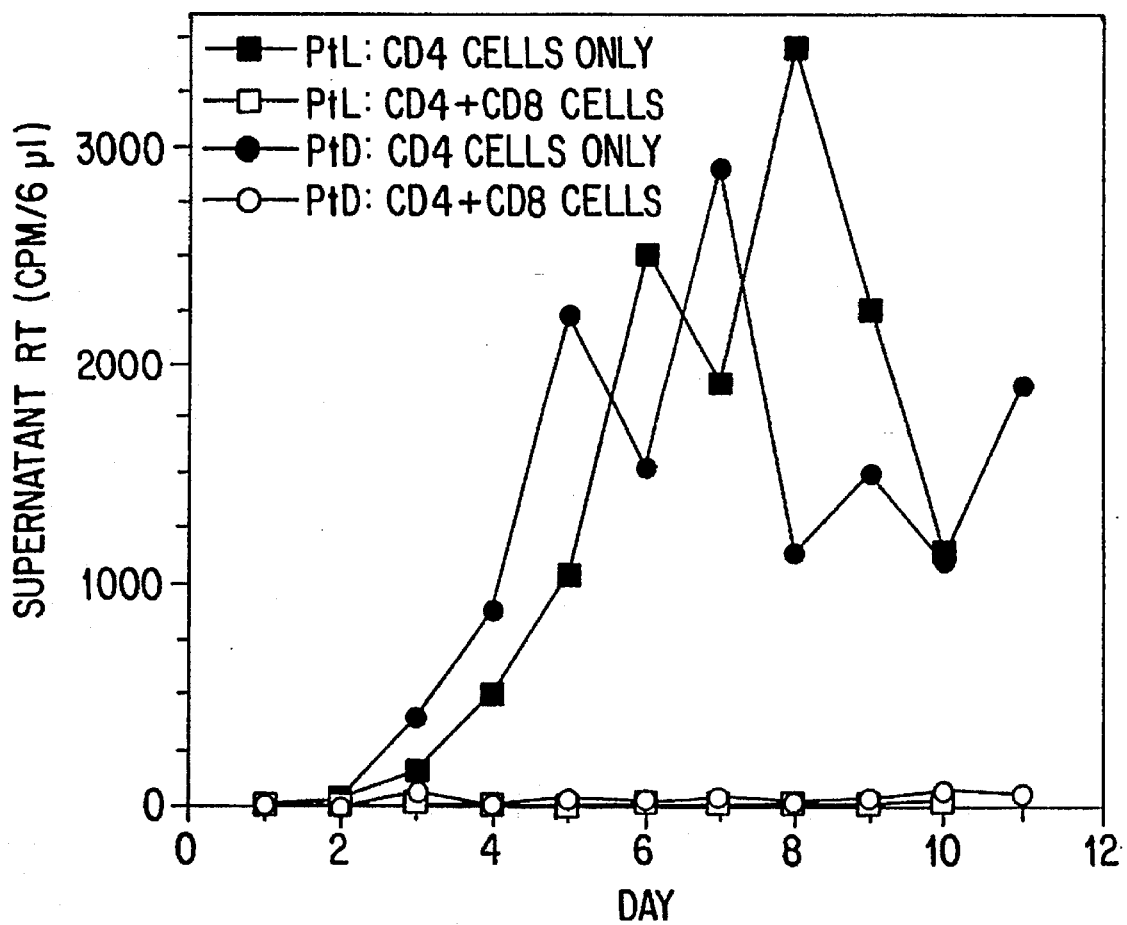
FIG. 1. CD8 Cells from HIV-1 Seropositive Individuals Suppresses virus production.

The effect of CD8 cells on HIV-1 replication was investigated by performing experiments in which CD8 cells, prepared from HIV-1 infected individuals by immunoaffinity techniques, were mixed with virally infected CD4+ cells in a 2:1 ratio. The inhibition of HIV-1 viral replication can be measured by determining the levels of reverse transcriptase activity in HIV-1 infected cells. As illustrated in FIG. 1, inhibition of viral replication was virtually complete in the presence of CD8 cells.

Figure 2:
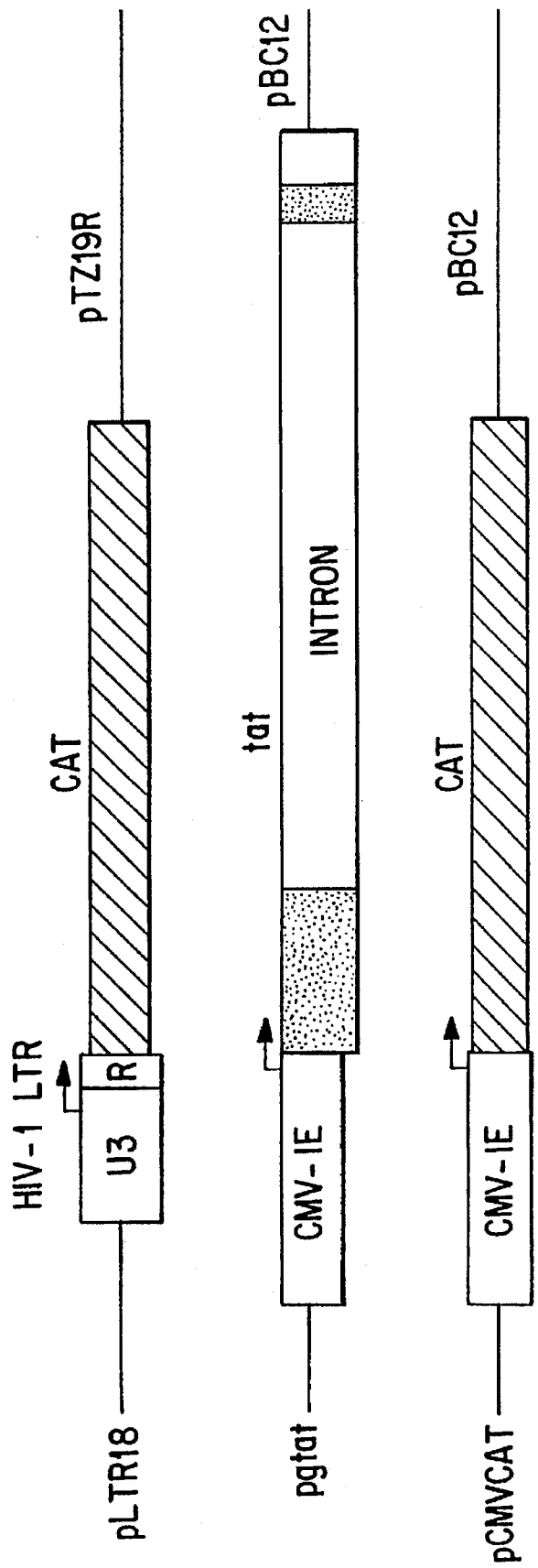
FIG. 2. Plasmid constructs used in HIV-1 LTR transcription assays.
Figure 3:
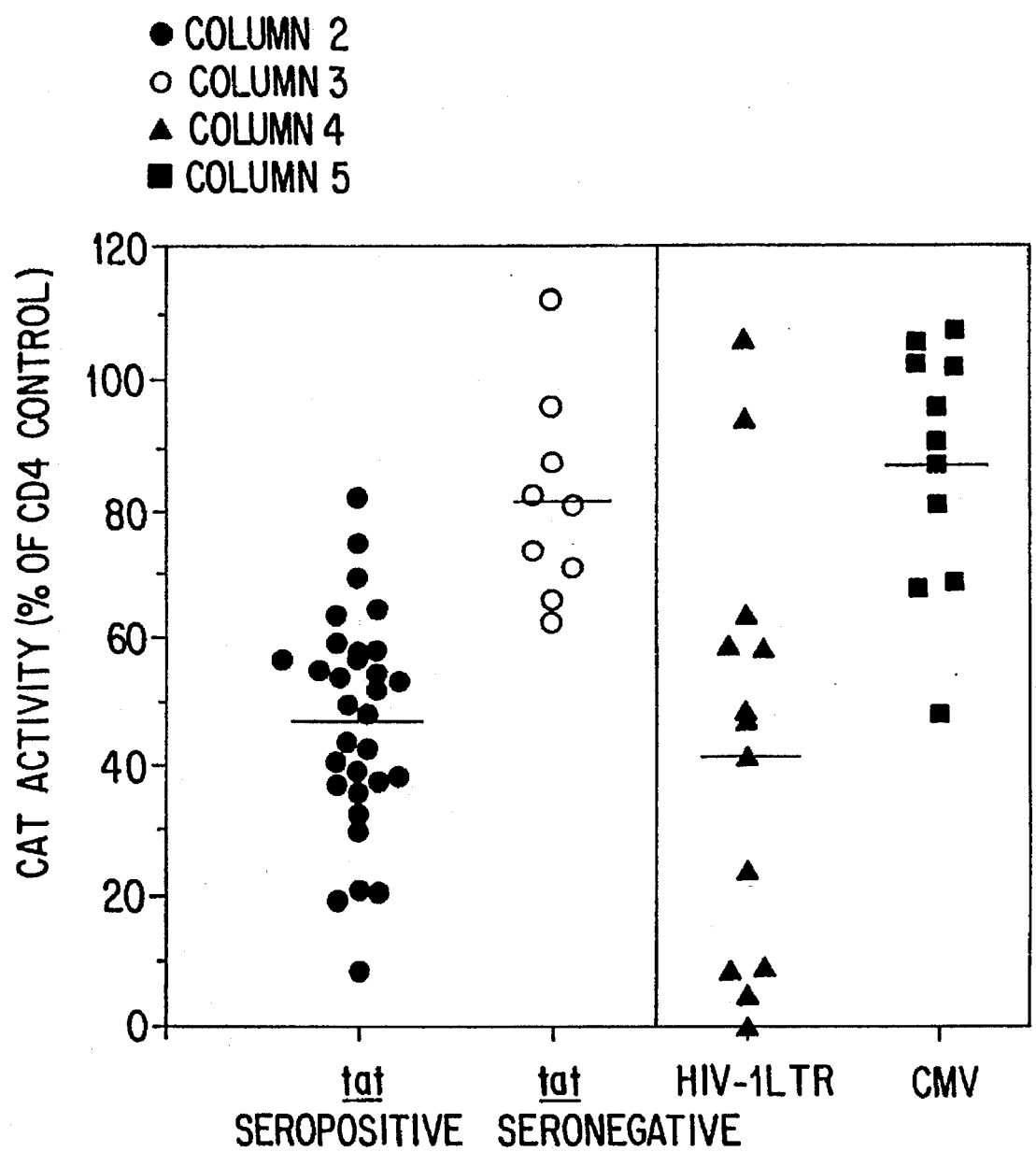
FIG. 3. CD8 Cells from HIV-1 infected individuals suppress HIV-1 LTR transcription. Data are plotted for CAT activity in cultures containing autologous CD8 cells compared to the activity measured in cultures derived from the same transfection containing autologous CD4 cells. Horizontal lines are drawn to indicate the means of each population.
Figure 4:
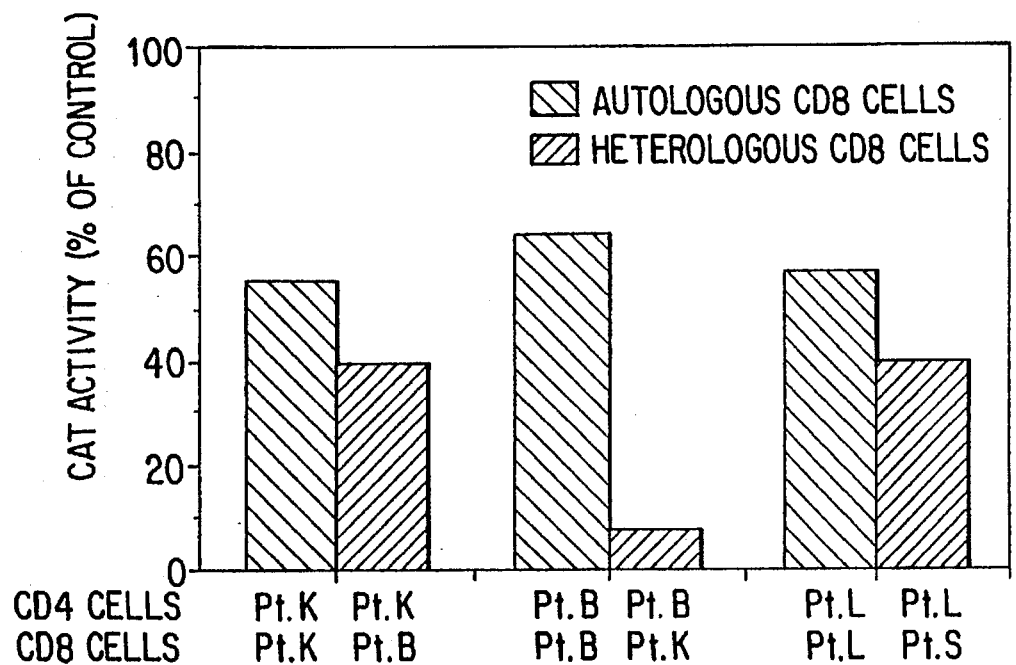
FIG. 4. CD8 cells suppress Tat-mediated transcription in heterologous CD4 cells. Data are plotted for CAT activity in cultures containing autologous or heterologous CD8 cells compared to the activity measured in cultures derived from the same transfection containing autologous CD4 cells.
Figure 5:
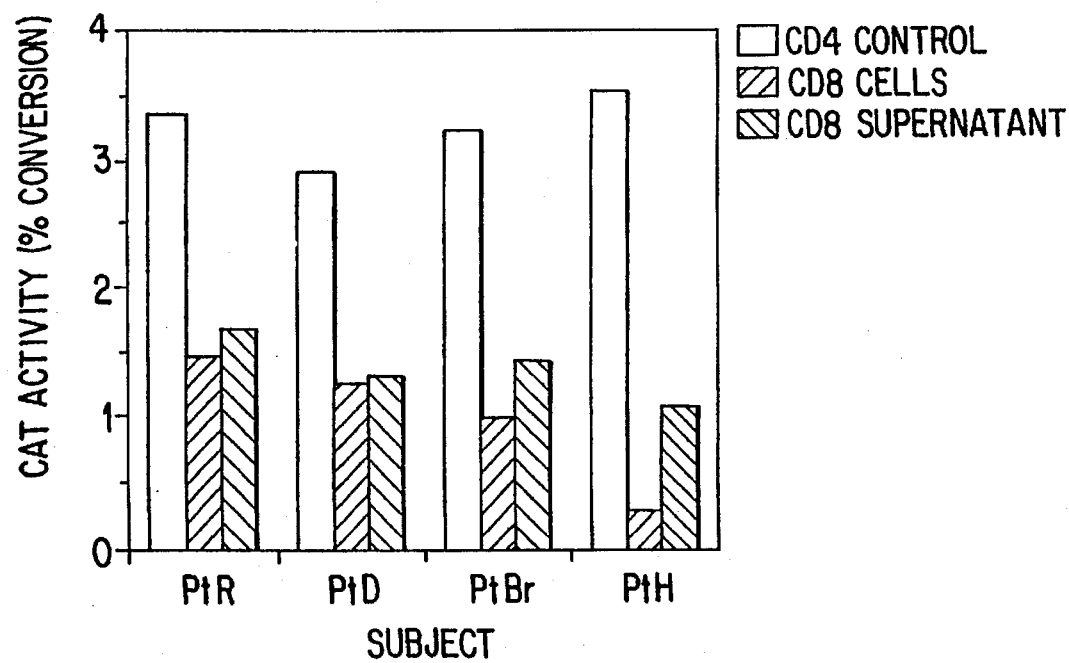
FIG. 5. A soluble factor from CD8 cells inhibits Tat-mediated transcription. CAT activity was measured in cultures containing autologous CD4 cells, cultures containing autologous CD8 cells and cultures containing autologous CD8 cell conditioned medium. Each data set from an individual subject was derived from a single transfection. CAT activity is expressed as percent conversion, each assay was based on $5 \times 10^6$ transfected CD4 cells.

Experiments were performed to test whether the mechanism by which the CD8+ suppressor molecule inhibits viral replication is through inhibition of viral gene transcription. A recombinant expression vector was constructed comprising the HIV-1 LTR promoter sequences cloned adjacent to the CAT reporter gene (FIG. 2). The construct was co-transfected into affinity purified CD4+ cells with a second construct expressing the product of the viral Tat gene which is required for viral transcription. A construct consisting of the CAT gene cloned adjacent to the cytomeglovirus immediate early promoter (CMV-IE, FIG. 2) was used as a control (FIG. 2). As indicated in FIG. 3, decreased levels of CAT activity were observed in the presence of autologous CD8+ cells, indicating inhibition of HIV-1 LTR and Tat-mediated HIV-1 LTR transcription in the autologous CD4+ infected cells. Similar experiments were carried out using hetrologoeous CD8 cells. When these cells were mixed with the transfected CD4 cells a decrease in CAT activity was also observed (FIG. 4) indicating that compatibility at the major histocompatability locus (MHC) is not required for HIV-1-suppressor activity. In addition, supernatants derived from CD8 cell culture exhibited inhibitory activity indicating that the antiviral activity is a soluble factor secreted by the CD8+ cells (FIG. 5).

In addition, other viruses of human and animal origin contain similar and/or identical promoter elements as those found in HIV, raising the possibility that the CD8 suppressor molecule may be of value in the treatment of other viral infections such as CMV, HIV-2, HTLV-1 and 2, FeLV, etc.

SUBSETS OF CD8+ CELLS EXPRESS ANTI-VIRAL ACTIVITY

The availability of CD8 cell clones expressing antiviral activity will permit extensive surface marker phenotyping of the cells producing this activity. Once the distinguishing phenotype(s) of these cells is established, improved immunoaffinity techniques for purifying these cells can be devised. If these cells play a role in maintaining the asymptomatic state during HIV infection, these markers may be useful for a) clinical staging of infected individuals, b) monitoring the effect of antiviral therapy on disease progression, c) monitoring the effectiveness of therapy with immunological/biological response modifiers, and d) monitoring vaccine response.

Such cell lines may also be used for purification and characterization of the suppressor molecule using methods and techniques described in Section 5.3., infra. The cell lines may also be used as a source of RNA from which cDNA libraries may be constructed as described in Section 5.4., infra.

Figure 6:
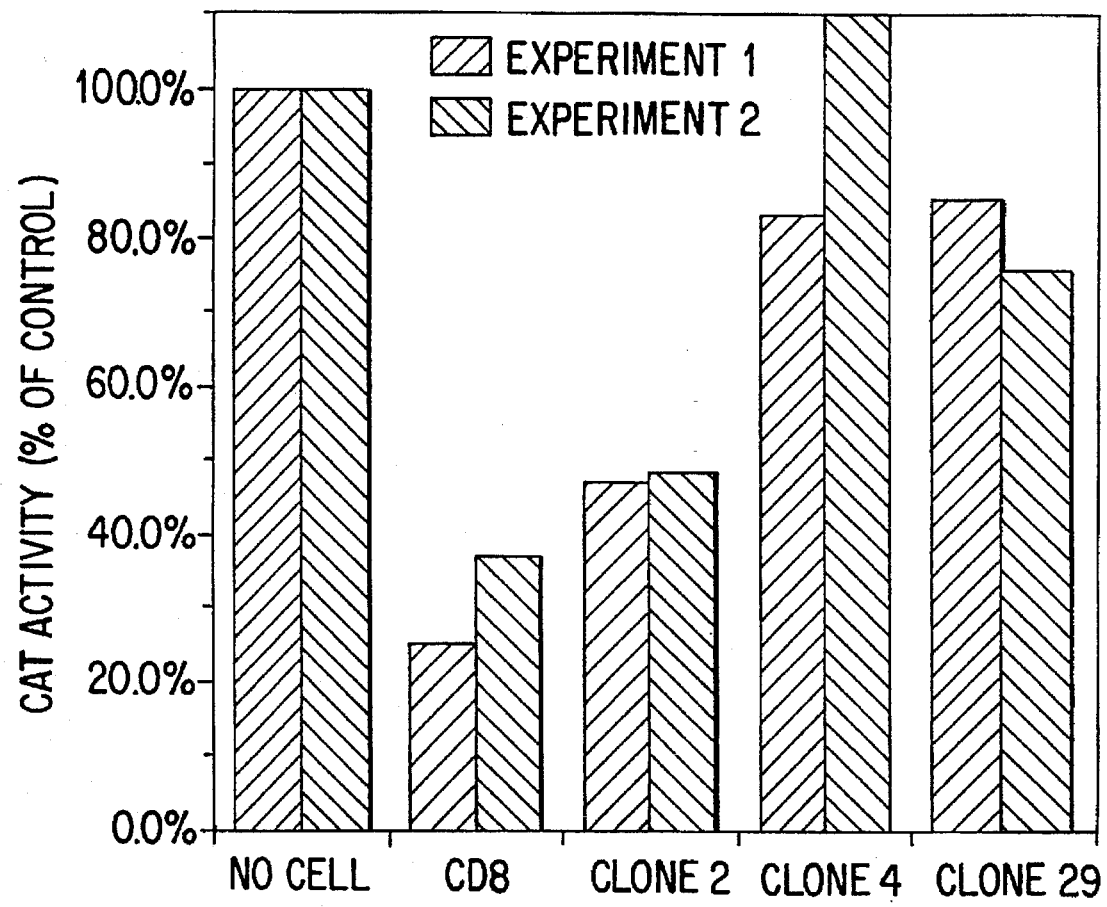
FIG. 6. HIV transcriptional inhibition is expressed by a primary CD8 cell clone.

In a specific embodiment, described herein, CD8 cells were immunoaffinity purified from the blood of an HIV infected patient and the purified CD8 cells were subjected to limited dilution cloning. The resulting CD8 primary cell clones were assessed for their ability to inhibit tat-mediated HIV LTR transcription in autologolous B-lymphocytes cell lines transfected with the tat encoding vector and the LTR/CAT expression vector. FIG. 6 shows the level of CAT inhibition observed for three CD8 primary cell clones. As indicated in the Figure, the clones exhibit varying degrees of inhibition of transcription. Clone 2 (DU. HL-1) shows the greatest inhibition of CAT activity while clone 4 (DU. HL-4) does not inhibit activity.

PURIFICATION AND CHARACTERIZATION OF CD8+ SUPPRESSOR MOLECULE

The CD8+ suppressor molecule is secreted by CD8+ cells. In addition, primary cell clones expressing the antiviral activity have been isolated (see Section 5.2., supra). The CD8 antiviral activity may be isolated from the conditioned media of such cells and subsequently purified to high specific activity. Purification of the CD8 suppressor molecule may be achieved utilizing various procedures and techniques known in the art which include but are not limited to chromatography (e.g., reverse phase liquid, gel permeation, liquid exchange, ion exchange, size exclusion, affinity chromatography), centrifugation, electrophoretic procedures, differential solubility, or by any other standard technique for the purification of proteins.

During any protein purification process, the success of the process depends on the availability of a reliable assay system for measuring the presence of the protein of interest. In an embodiment of the invention, inhibition of HIVI-LTR and/or Tat dependent HIV transcription may used as an indicator of CD8 suppressor activity. For example, a recombinant expression vector may be engineered to contain the HIV LTR promoter sequences cloned adjacent to a reporter gene and suppressor activity may be measured by assaying for reporter gene activity. Reporter genes that may be used include, but are not limited to those encoding chloramphenicol acetyltransferase (CAT), firefly luciferase or human growth hormone. In the assay system described here, the LTR/reporter gene constructs are co-transfected into an appropriate cell line using transfection methods such as, for example, calcium phosphate transfection, DEAE-dextran transfection, electroporation or liposome-mediated transfection. The transfected cells may then be used to test for the presence of antiviral activity. In a specific embodiment described herein, the HIV-LTR sequences were cloned adjacent to the CAT gene, the construct was transfected into infected CD4 cells and the presence of CD8 antiviral activity was determined by measuring CAT activity (FIG. 3 and FIG. 4).

Using standard techniques for protein purification and the assay system described above, the CD8 suppressor protein may be purified to homogeneity. Once purified, the CD8+ protein may be subjected to microsequencing, using techniques routinely used by those skilled in the art to determine the amino acid sequence of a protein ( see, Current Protocols in Molecular Biology, Ausubel et al., Green Publishing Associates and Wiley Intersciences, N.Y.) If the CD8 suppressor molecule is blocked at the amino terminus, the protein may be chemically cleaved or partially enzymatically digested to yield peptide fragments that may be purified and sequenced.

The purified CD8+ protein may be used for production of antibodies to epitopes of the CD8+ protein. Such antibodies include but are not limited to polyclonal and monoclonal antibodies. For production of antibodies, various host animals may be immunized by injection with the CD8+ protein including but not limited to rabbits, mice, rats etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to CD8 suppressor molecule may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used.

Antibody fragments which contain specific binding sites of the CD8 suppressor molecule may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

Alternatively, Fab expression libraries may be constructed (Huse et al., 1989, Science, 246:1275–1281) to allow rapid and easy identification of monoclonal Fab fragments with the desired specificity to the CD8 supressor molecule.

5.4. CLONING OF CD8+ SUPPRESSOR MOLECULE

The present invention relates to methods for cloning of the CD8 suppressor molecule. Using methods which are well known to those skilled in the art, recombinant cDNA libraries may be constructed using RNA prepared from cells known to express the CD8 suppressor molecule. The cDNA libraries may be constructed using a variety of vector systems, including but not limited to, bacteriophage vectors, plasmid vectors or mammalian expression vectors. See, for example, the techniques described in Sambrook et al., 1989, Molecular Cloning: A Laboratory Manual, Cold Spring Harbor Laboratory, N.Y. and Current Protocols in Molecular Biology, Green Publishing Associates and Wiley Intersciences, N.Y.

The recombinant cDNA libraries may be screened using a number of different techniques. For example, a mixture of degenerate oligonucleotide probes may be designed utilizing the information derived from protein sequencing of the CD8 suppressor protein (see Section 5.3 supra). The oligonucleotides may be labeled and used directly to screen a cDNA library for clones containing inserts with sequence homology to the oligonucleotide sequences. Alternatively, the oligonucleotides may be used as primers in a polymerase chain reaction. The template for the reaction is cDNA obtained by reverse transcription of mRNA prepared from cells known to express the suppressor activity. The amplified DNA fragment may be labeled and used to screen a library for isolation of full length clones. In another example, an expression library may be screened immunologically using polyclonal or monoclonal antibodies directed against the CD8 suppressor molecule. In yet another embodiment of the invention, a cDNA library may be engineered into a mammalian expression vector and screened by transfection into the appropriate mammalian cell line followed by assaying for anti HIV suppressor activity in the tissue culture supernatant.

In a preferred embodiment of the invention, a subtracted cDNA library may be constructed using RNA prepared from expressing and non-expressing clonal CD8 cells. The subtracted library may be screened using the LTR/reporter gene assay system. A subtracted cDNA library contains cDNA clones corresponding to mRNAs present in one cell type ([+]cell type) that are not present in a second cell type ([−]cell type). Construction of this type of library enriches for cDNA clones of interest and is used in the isolation of a cDNA clone corresponding to a particular mRNA where the screening procedure is laborious because a specific DNA sequence or antibody is unavailable.

In an embodiment of the invention a subtractive library may be constructed using mRNA prepared from the expressing [+]and non-expressing [−]clonal CD8 cell lines (see Section 5.2., supra). The [+]cDNA is prepared from cells expressing the antiviral activity and oligonucleotide linkers are ligated onto the ends of the cDNA fragment resulting in endonuclease recognition sites on each end of the cDNA fragment. The [−]cDNA is prepared with blunt ends and digested with a restriction endonuclease that reduces the [−]cDNA fragments to small blunt ended fragments. The [+]cDNA is then mixed with a 50-fold excess of fragmented [−]cDNA, the DNAs are heated to melt apart the double-stranded DNA, and the single stranded DNA is allowed to reanneal. The only [+]cDNA likely to regenerate double stranded fragments with restriction endonuclease restriction sites at each end are those sequences for which no complementary [−]fragments were present. Annealed fragments are ligated in an expression vector having complementary cohesive ends. The resulting cDNA library may be screened using the LTR/CAT expression system.

USES OF THE CD8+ SUPPRESSOR MOLECULE

Currently approved treatments for HIV infection and acquired immunodeficiency disease are pharmaceuticals such as dideoxynucleosides that target viral reverse transcriptase (i.e. AZT, ddI, ddC). Though some clinical benefit has been demonstrated for these agents, drug resistant viral mutants arise limiting their usefulness. Moreover, these agents are only effective against de novo infection and do not exert an antiviral effect against chronically infected or latently infected cells. More effective treatments for HIV infection and AIDS are greatly needed.

The CD8 subclass of T-lymphocytes produce a molecule that inhibits HIV replication suggesting the potential usefulness of this molecule as a therapeutic for treatment of HIV infection and acquired immunodeficiency disease. Because of the ability of the CD8+ molecule to prevent virus production in cells already infected, it may be of use prophylactically in settings such as vertical transmission of HIV from mother to infant or in acute exposure to HIV.

Because the molecule may play a role in maintaining the asymptomatic state of HIV infected individuals, it may be of use for clinical staging of disease progression, monitoring the effects of immune or biological response modifier therapy and for assessing effectiveness of certain vaccination protocols.

EXAMPLE: CD8 SUPPRESSOR ACTIVITY INHIBITS HIV-1 REPLICATION

MATERIALS AND METHODS

REVERSE TRANSCRIPTASE ASSAYS

Peripheral blood mononuclear cells (PBMC) were prepared from freshly-drawn, anticoagulated blood by standard Ficoll-Hypaque density separation. CD4 and CD8 lymphocytes were purified by attachment to antiCD-4 and anti-CD8 microCellector flasks (Applied Immune Sciences) according to the manufacturers recommendations, washed extensively, and cultured for 3 days in medium containing RPMI 1640, 20%, v/v fetal calf serum, 50 U/ml recombinant IL-2 (Hoffman LaRoche, Inc.) 50 µg/ml gentamicin sulfate, and 3 µg/ml phytohemagglutinin (PHA, Sigma, Inc.). Cells were removed from the microCellector flasks, aliquots of the CD4 and CD8 cell suspensions were analyzed for relative purity by FACS analysis and cell viability was determined by vital dye exclusion. The remaining cell suspensions were cultured for an additional 24 hr in the same medium as above but lacking PHA. CD4 cells were adjusted to $2\times10^6$ cells/ml and 100 µl aliquots were cultured in duplicate or triplicate wells of 96-well microtiter plate with 100 µl of fresh medium or 100 µl of autologous CD8 cells (adjusted to $4\times10^6$ cells/ml), and cultures were incubated at 37° C. in a humidified $CO_2$ incubator. At 24 hr intervals 100 µl aliquots of cultures supernatants were taken, adjusted to 1% Triton X-100 and assayed for reverse transcriptase (RT) activity as described below or frozen at −70° C. until assayed. The cultures were fed with 100 µl of fresh medium each time supernatants were harvested. RT activity was assayed by a modification of the published methods of Goff et al., and Willey et al. 10 µl of triton lysate was mixed with 50 µl of a reaction cocktail containing 50 mM Tris-HCl. pH 7.8, 75 mM KCl, 2 mM DTT, 5mM $MgCl_2$, 5 µg/ml Poly A, 1.5 µ/ml OligodT$_{12-18}$, 0.05% NP-40, and 10 µCi/ml 32P-TTP, and incubated at 37° C. for 90 min. 40–50 µl aliquots of reaction mixtures were spotted onto either DE-81 paper (Whatmann) or onto NA-45 membranes (Schleicher & Schuell) in a manifold sample filtration manifold (Schleicher & Schuell), and the membranes or paper were washed several times with 2×SSC (0.3M NaCl, 0.03M NaCitrate), followed by 2×SSC containing Bromophenol blue to locate spots. Autoradiography was performed, and the membranes or DE-81 paper counted using a Packard Matrix 9600 Direct Beta Counter. Results presented are the means of duplicate or triplicate wells.

HIV-1 LTR CAT CONSTRUCTS

The plasmids used in these studies were as follows: 1) pLTR 18, constructed by inserting the XhoI-BamHI LTR-CAT containing fragment of pU3RIII (Rosen C. A., Sodroski J. G., Haseltine W. A., 1985) into pTZ19R (United States Biochemical) at the HindIII site by blunt-end ligation. Expression of the chloramphenicol acetyl transferase (CAT) reporter gene in this vector is under the control of the HIV-1 LTR promoter; 2) pgtat, a tat expression vector under the control of the CMV-IE promoter (Malim M. H., Hauber J., Fenrick R., Cullen B. R., 1988); 3) pCMVCAT (kindly provided by Dr. B. Cullen, Duke University Medical Center), expression of the CAT reporter gene in this vector is under the control of the same CMV-IE promoter present in the pgtat vector.

TRANSFECTIONS AND CAT ASSAYS

Purified populations of CD4 and CD8 lymphocytes were prepared from freshly-drawn anticoagulated blood as described in Section 6.1.1., except that purified CD4 and CD8 cells were expanded in culture for 2-5 days prior to setting up the transfection. To assess effects of CD8 cells on HIV-1 LTR or CMV-IE transcriptional activity, CD4 lymphocytes ($20\times10^6$ cells) were transfected with 10 µg of plasmid (either pLTR 18 or pCMVCAT) by electroporation using a Bio-Rad Gene Pulser. To assess effects on tat-mediated HIV-1 LTR transcription. $20\times10^6$ CD4 lymphocytes were transfected by electroporation with 2 µg pgtat and 10 µg pLTR 18. The protocol used for the transfections was previously described by Cann et al. The settings used for electroporation were 960 µF, 250 V for a single pulse. 4 ml aliquots of CD4 cells in fresh medium ($1.25\times10^6$ cells/ml) from a single transfection were aliquoted into 4 flasks containing either an equal volume of autologous CD4 cell conditioned medium, an equal volume of autologous CD4 cell conditioned medium containing $10\times10^6$ non-transfected autologous CD4 cells, an equal volume of autologous CD8 cell conditioned medium, or an equal volume of autologous CD8 cell conditioned medium containing $10\times10^6$ autologous CD8 cells. The volume of each flask was adjusted to 10 ml with a combination of fresh medium (RPMI 1640, 10% heat inactivated fetal calf serum, 5% IL-2 (Cellular Products, Inc.) and 1% Pen-Strep (Gibco)), and either autologous CD4 or CD8 cell conditioned medium so that the final concentration of conditioned medium in each flash was 50%. Cultures were incubated for 48 hr at 37° C. in a humidified $CO_2$ incubator. Cultures were harvested, and CAT activity was determined essentially as described by Ballard et al., except that 1% Triton X-100 was added to the cell disruption buffer which contained 100 mM Tris-HCl, pH 7.8. CAT activity was not affected by the presence of 1% Triton X-100. Data are plotted for CAT activity in cultures containing autologous CD8 cells compared to the activity measured in cultures derived from the same transfection containing autologous CD4 cells. Horizontal lines are drawn to indicate the means of each population. To test tat-mediated transcription in heterologous CD4 cells a flask containing heterologous CD8 cell conditioned medium and $10\times10^6$ heterologous CD8 cells was substituted in each transfection. Data are plotted for CAT activity in cultures containing autologous or heterologous CD8 cells compared to the activity measured in cultures derived from the same transfection containing autologous CD4 cells.

CAT activity was measured in conditioned medium removed from cultures containing autologous CD4 cells, cultures containing autologous CD8 cells and cultures containing autologous CD8 cells. Each data set from an individual subject was derived from a single transfection. CAT activity is expressed as percent conversion, each assay was based on $5\times10^6$ transfected CD4 cells.

RESULTS

CD8 CELLS INHIBIT HIV-1 REPLICATION IN CD4 HIV INFECTED CELLS

CD8 cells prepared from HIV-1 infected individuals by immunoaffinity techniques and stimulated with PHA, inhibit HIV-1 replication in autologous, infected CD4 cells. The potency of the antiviral effect is striking. When CD8 cells are incubated with CD4 cells in a 2:1 ratio, inhibition of viral replication is virtually complete as measured by reverse transcriptase (FIG. 1).

To investigate the mechanism of CD8 antiviral activity the effect of CD8 cells on HIV-1 transcription was examined. Autologous and heterologous PBMC-derived CD4 cells were transfected by electroporation with an HIV-1 LTR CAT construct and a construct that expresses the product of the tat gene. CAT activity was measured in the presence of CD8 cells and as illustrated in FIG. 3 and 4, CD8 cells from HIV-1 infected individuals inhibit tat-mediated HIV-1 LTR transcription in autologous and heterologous CD4 cells. Experiments conducted with supernatants derived from CD8 cell cultures indicate that a significant fraction of the inhibitory activity can be found in the supernatant indicating that the suppressor activity is secreted by CD8 cells (FIG. 5).

EXAMPLE: ISOLATION OF CD8 CLONAL CELLS EXPRESSING THE ANTI-HIV-1 SUPPRESSOR MOLECULE

MATERIALS AND METHODS

ESTABLISHMENT OF CD8+ CELL CLONES

Peripheral blood mononuclear cells (PBMC) were prepared from freshly-drawn, anti-coagulated patient blood by standard Ficoll-Hypaque density separation. Twenty million washed PBMC were incubated with anti-CD8+ bound magnetic microspheres (Dynal, Inc.) at a bead:cell ratio 10:1 in RPMI 1640+1% FCS. After 45' incubation at 5° C. (with occasional resuspension), CD8 cell/microsphere conjugates were captured on a rare earth magnet, washed twice, and recaptured. The conjugates were transferred to a T-25 tissue culture flask containing 10 ml of RPMI 1640, 20% v/v fetal calf serum. 50 mg/ml of gentamicin sulfate, 3 mg/ml phytohemagglutinin (PHA: Sigma, Inc.) and 50 U/ml recombinant interleukin 2 (IL-2; Hoffman LaRoche, Inc.) Conjugates were incubated at 37° C., 5% $CO_2$ for 48 hours, after which the microspheres were removed by magnetic capture. The remaining CD8+ cells in suspension were analyzed for relative purity by FACS analysis and cell viability was determined by vital dye exclusion. Suspensions of 102 viable CD8+ cells were subjected to limited dilution cloning as follows. All wells of a single 96-well round-bottom plate received 10 cells per well, two 96-well plates were seeded at 1 cell/well, and five 96-well plates were seeded at 0.1 cell/well. All wells of all 8 plates subsequently received $2\times10^5$ irradiated (6000R) heterologous PMBC feeders in the presence of 200 ng/ml anti-CD3 monoclonal antibody (12F6) and 100U/ml of IL-2. Plates were incubated at 37° C., 5% $CO_2$. At 14d intervals, 100 uL of cell-free supernatant was removed and discarded. Wells were re-fed with 100 uL of fresh media containing 20% FCS, 200 ng/ml 12F6, and 100 U/ml IL-2 containing $10^5$ irradiated (6000R) heterologous PMBC feeders. Wells exhibiting macroscopic evidence of cellular proliferation were selected for stepwise expansion into 48-well and 24-well plates and eventually T-25 and T-75 flasks. A 14d re-stimulation cycle was utilized throughout the expansion of the clonal populations of CD8+ cells. Periodic FACS analyses were performed using an extensive marker panel. Twenty-four hours prior to assay, dead feeder cells were removed by Ficoll-Hypaque sedimentation.

ASSAY OF TRANSCRIPTIONAL INHIBITION ACTIVITY IN CD8 CELL CLONES

CD8 cells clones were assessed for their ability to inhibit tat-mediated HIV-1 LTR transcription in autologous B lymphocyte cell lines (BLCL) transfected with pgtat and pLTR 18 as follows. Autologous B lymphocyte cell lines were prepared as follows. Peripheral blood was obtained from HIV-1 infected individuals and PBMCs were prepared by Ficoll-Hypaque density gradient separation. Seven to ten million cells were placed in a T-25 flask (Coaster) in 4 ml of cell culture medium (CCM: RPMI 1640, 20% v/v fetal calf serum, 50 µg/ml gentamicin). One ml of EBV supernatant harvested from a marmoset cell line (B95-8; ATCC) and 10 µg of cyclosporin A were added to the cell suspension. The flasks were incubated undisturbed at 37° C. in a humidified $CO_2$ incubator for 3–6 weeks. Once a stably transformed BLCL was established it was resuspended in CCM at a concentration of 3×105 cells/ml. Routine cell culture maintenance entailed centrifugation and resuspension in new CCM every 2–3 days. In this manner, exponential growth was obtained with cell viability routinely 85–90%. Autologous BLCL were cotransfected with 0.1 µg pgtat/106 BLCL and 0.5 µg pLTR 18/106 BLCL as described in the legend to FIG. 2. Transfected BLCL were aliquoted ($1.5 \times 10^6$ cells) into flasks containing either 50% BLCL conditioned medium, $3 \times 10^6$ autologous CD8 cells with 50% autologous CD8 cell conditioned medium (experiment 1) or $3 \times 10^6$ heterologous CD8 cells with 50% heterologous CD8 cell conditioned medium (experiment 2), or $3 \times 10^6$ autologous CD8 clone 2 cells with 50% clone 2 cell conditioned medium, or $3 \times 10^6$ autologous CD8 clone 4 cells with 50% clone 4 cell conditioned medium, or $3 \times 10^6$ autologous CD8 clone 29 cells with 50% clone 29 cell conditioned medium. The final volume of each culture was adjusted to 10 ml, and cultures were incubated for 48 hr at 7° C. in a humidified $CO^2$ incubator. Cultures were harvested, and CAT activity was assayed as described in the legend to FIG. 2. Data are presented for CAT activity determined in cultures containing CD8 cells or CD8 clones compared to cultures only containing transfected BLCL.

RESULTS

ESTABLISHMENT OF CD8 CELL CLONES EXPRESSING THE HIV-1 SUPPRESSOR MOLECULE

Peripheral blood mononuclear cells (PBMC) were prepared from a HIV-1 infected blood. CD8 cells were immunoaffinity purified from the patient's blood and he purified cells were subjected to dilution cloning. The resulting cell clones were assessed for their ability to inhibit HIV-1 LTR transcription in autologous B-lymphocyte cell lines transfected with the HIV-1 LTR CAT and tat encoding constructs. As demonstrated in FIG. 6, the cell clones (clone 2, 4 and 29) vary in their ability to inhibit CAT activity. Clone 2 (DU. HL-2) exhibits the greatest inhibitory activity with clone 4 (DU. HL-4) not inhibiting CAT activity to any significant degree.

DEPOSIT OF MICROORGANISMS

The following microorganisms have been deposited with the American Type Culture Collection, (ATCC), Rockville, Md. and have been assigned the following accession numbers:

| Microorganism | Date of Deposit | Accession No. |
| --- | --- | --- |
| DU. HL-2 | March 26, 1993 | CRL 11310 |
| DU. HL-4 | March 26, 1993 | CRL 11309 |

The present invention is not to be limited in scope by the microorganisms deposited since the deposited embodiments are intended as illustrations of single aspects of the invention and any microorganisms which are functionally equivalent are within the scope of the invention.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. A method for detecting a CD8 suppressor molecule that has anti-HIV activity, comprising:
    (a) culturing a host cell line transfected with a recombinant DNA expression vector in which a reporter gene is operatively associated with an HIV LTR promoter sequence;
    (b) contacting the cell line with a sample comprising enriched CD8 cells or cell cultures of CD8 cells; and
    (c) measuring the inhibition of reporter gene activity, wherein inhibition of reporter gene activity correlates with anti-HIV activity.

2. A diagnostic assay for monitoring the clinical progression of HIV infection comprising:
    (a) collecting successive blood samples from an HIV infected individual;
    (b) culturing a host cell line transfected with a recombinant DNA expression vector in which a reporter gene is operatively associated with an HIV LTR promoter sequence;
    (c) contacting the cell line with the samples from the HIV infected individual;
    (d) measuring the inhibition of reporter gene activity, wherein inhibition of reporter gene activity correlates with anti-HIV activity; and
    (e) comparing the inhibition of reporter gene activity in each of the samples wherein a decrease in reporter gene activity in each of the successive samples indicates progression of HIV infection.

3. The method of claim 1 or 2 in which the reporter gene is the chloramphenicol acetyltransferase gene.

4. The method of claim 1 or 2 in which the reporter gene is the firefly luciferase gene.

5. The method of claim 1 or 2 in which the reporter gene is the human growth hormone gene.

* * * * *